United States Patent [19]

Brendler et al.

[11] Patent Number: 5,416,232
[45] Date of Patent: May 16, 1995

[54] CATALYST FOR DISPROPORTIONATING ARYL- OR ALKYHALODISILANES INTO ARYL- OR ALKYLHALOMONOSILANES AND ARYL- OR ALKYLHALOPOLYSILANES

[75] Inventors: Erica Brendler; Gerhard Roewer, both of Freiberg, Germany

[73] Assignee: Solvay Deutschland GmbH, Hanover, Germany

[21] Appl. No.: 192,622

[22] Filed: Feb. 7, 1994

[30] Foreign Application Priority Data

Feb. 12, 1993 [DE] Germany .................. 43 04 256.2

[51] Int. Cl.⁶ ................................. C07F 7/08
[52] U.S. Cl. .................... 556/469; 556/474; 502/167
[58] Field of Search ............. 556/474, 469; 502/167

[56] References Cited

U.S. PATENT DOCUMENTS

| | | | |
|---|---|---|---|
| 2,834,648 | 5/1958 | Bailey et al. | 556/469 |
| 4,082,767 | 4/1978 | Yamahara et al. | 502/167 UX |
| 4,347,351 | 8/1982 | Swart | 502/167 UX |
| 4,393,009 | 7/1983 | Freitag et al. | |
| 4,548,917 | 10/1985 | Lepage et al. | 556/469 X |
| 4,567,286 | 1/1986 | Lepage et al. | 556/469 |
| 4,746,752 | 5/1988 | Lepage et al. | 556/469 |
| 4,870,200 | 9/1989 | Ottlinger et al. | |
| 4,950,635 | 8/1990 | Williams et al. | 502/167 UX |
| 5,252,768 | 10/1993 | Geisberger et al. | 556/469 |
| 5,260,246 | 11/1993 | Yuo et al. | 502/167 |
| 5,274,114 | 12/1993 | Weider et al. | 502/167 UX |
| 5,288,892 | 2/1994 | Pachaly et al. | |

FOREIGN PATENT DOCUMENTS

| | | |
|---|---|---|
| 021373 | 1/1981 | European Pat. Off. . |
| 074837 | 3/1983 | European Pat. Off. . |
| 138670 | 4/1985 | European Pat. Off. . |
| 286074 | 10/1988 | European Pat. Off. . |
| 574912 | 12/1993 | European Pat. Off. . |

OTHER PUBLICATIONS

Hackh's Chemical Dictionary, 4th Ed., McGraw-Hill Book Company, 1969, pp. 87 & 340.

Primary Examiner—Paul F. Shaver
Attorney, Agent, or Firm—Evenson, McKeown, Edwards & Lenahan

[57] ABSTRACT

Catalysts composed of nitrogen-containing heterocyclic hydrocarbons, optionally fixed to a support material, for disproportionating aryl- and alkylhalodisilanes into the corresponding mono- and polysilanes, and a process of using these catalysts for disproportionating disilanes.

23 Claims, No Drawings

CATALYST FOR DISPROPORTIONATING ARYL- OR ALKYHALODISILANES INTO ARYL- OR ALKYLHALOMONOSILANES AND ARYL- OR ALKYLHALOPOLYSILANES

BACKGROUND OF THE INVENTION

The invention relates to catalysts for the disproportionation of aryl- or alkylhalodisilane into aryl- or alkylhalomonosilane and aryl- or alkylhalopolysilane, and also to a process for the disproportionation of aryl- or alkylhalodisilanes using these catalysts.

Aryl- and alkylhalosilanes, i.e. silanes substituted by aryl or alkyl groups and halogen atoms, in particular methylchlorosilanes, are valuable industrial starting materials for producing silicone products.

Methylchlorosilanes such as dichlorodimethylsilane and trichloromethylsilane are prepared, inter alia, by the Mueller-Rochow synthesis. However, this produces, after distillation of the products, relatively high-boiling residues in amounts of up to 10% by weight. From these distillation residues there can be obtained a fraction which boils in the temperature range of about 150° C. to 160° C. and which essentially comprises alkylhalodisilanes, such as methylchlorodisilanes. From both economic and ecological points of view it is desirable to be able to work up the distillation residues and thus achieve complete utilization of the raw materials used. Previously known processes for catalytic disproportionation of, for example, methylchlorodisilanes into monomeric methylchlorosilanes and methylchloropolysilanes preferably use as catalytically active substances

- amines, for example $NR_3$ where $R=H$, alkyl, aryl, and also the corresponding quaternary ammonium salts
- quaternary phosphonium salts
- hexamethylphosphoramide (HMPA)
- cyanides, in particular silver cyanide.

Disadvantages of these catalytically active substances include, for example, a low activity or the fact that long reaction times are required, which results in polysilanes which, despite the long reaction times, often have a very syrupy consistency, which can be attributed to a high proportion of relatively low molecular-weight polysilanes and which makes their further processing difficult and leads to low yields on conversion into ceramic products. In addition, the proportion and the composition of the monosilane fraction obtained can only be varied within narrow limits.

On the other hand, for example, the use of HMPA cannot be approved without question because of its physiologically questionable nature, despite its good catalytic properties. Despite the efforts of the prior art, there remains a need for improved catalysts for disproportionating aryl- and/or alkylhalodisilanes to monosilanes and polysilanes.

SUMMARY OF THE INVENTION

It is therefore the object of the invention to provide improved catalysts for disproportionating aryl- and/or alkylhalodisilanes and a process for using such catalysts to produce monosilanes and polysilanes.

Another object of the invention is to provide a catalyst for disproportionating aryl- and/or alkylhalodisilanes which exhibits high activity and selectivity.

A further object of the invention is to provide a catalyst for disproportionating aryl- and/or alkylhalodisilanes which is ecologically less objectionable.

It is also an object of the invention to provide a catalyst and process for disproportionating aryl- and/or alkylhalodisilanes which facilitate control of the composition of the disproportionation products by adjusting the process parameters.

These and other objects of the invention are achieved by providing a catalyst for disproportionating aryl- or alkylhalodisilanes, which catalyst comprises a nitrogen-containing heterocyclic hydrocarbon having at least one nitrogen atom in at least one 4- to 8-membered hydrocarbon ring, in which ring atoms adjacent the at least one nitrogen atom are selected from the group consisting of carbon atoms and nitrogen atoms.

In accordance with further aspects of the invention, the objects are achieved by providing a process for catalytically disproportionating an aryl- or alkylhalodisilane to form monosilanes and polysilanes comprising contacting the aryl- or alkylhalodisilane at a temperature in the range from 50° C. to 350° C. with a catalyst comprising a nitrogen-containing heterocyclic hydrocarbon having at least one nitrogen atom in at least one 4- to 8-membered hydrocarbon ring, wherein ring atoms adjacent the at least one nitrogen atom are selected from the group consisting of carbon atoms and nitrogen atoms, whereby the aryl- or alkylhalodisilane reacts to form monosilanes and polysilanes, and recovering the resulting monosilanes and polysilanes.

The invention thus relates to catalysts for the catalytic disproportionation of disilanes into mono- and polysilanes which catalysts are notable for high activity and selectivity and are ecologically less questionable, and with which the composition of the disproportionation products can be controlled by modification of the process parameters, and also to a process for carrying out the disproportionation using these catalysts.

DETAILED DESCRIPTION OF PREFERRED EMBODIMENTS

The catalyst according to the invention comprises a heterocyclic hydrocarbon having at least one nitrogen atom in at least one hydrocarbon ring, in which the positioning of the nitrogen ensures sufficient polarity of the molecule. The heterocyclic hydrocarbons of the invention have at least one nitrogen atom in at least one 4- to 8-membered hydrocarbon ring, where the ring atoms adjacent to the nitrogen can be carbon or nitrogen and the hydrocarbon ring or rings are, independently of one another, aromatic or non-aromatic hydrocarbon rings.

The nitrogen in the hydrocarbon ring can be substituted by

- H
- alkyl, branched or linear, preferably $C_1$ to $C_6$-alkyl
- oxygen
- halogen
- trialkoxysilyl
- $NR_2$, in which $R=H$, $C_1$ to $C_6$-alkyl, linear or branched, or trialkoxysilyl or be bonded in the ring via 2 sigma and 1 $\pi$ bond or can form the bridgehead to a further ring.

Depending on the bonding to the adjacent ring atoms, the carbon in the hydrocarbon ring can be mono- or disubstituted by

- H
- alkyl, branched or linear, preferably $C_1$ to $C_6$-alkyl halogen
oxygen
NR$_2$, in which R=H, C$_1$ to C$_6$-alkyl, linear or branched, or trialkoxysilyl or carry a further hydrocarbon ring system or it forms the bridgehead to a further ring system.

The substituents can, independently of one another, be identical or different. Nitrogen-containing heterocyclic hydrocarbons which are particularly suitable according to the invention as catalytically active substances for the disproportionation of aryl- and/or alkylhalodisilanes are, for example, 5-membered rings having from 1 to 3 nitrogen atoms in the hydrocarbon ring, preferably imidazole, 1-methylimidazole, 2-methylimidazole, pyrazole, 3-methylpyrazole, pyrrolidone, N-methylpyrrolidone, 1,3-dimethyl-2-imidazolidone or triazole or 6-membered rings having at least one nitrogen atom in the hydrocarbon ring, preferably 2,2'-bipyridine, 1,3-dimethyl-3,4,5,6-tetrahydro-2(1H)pyrimidone or N,N-dibutylpiperazine or polycyclic hydrocarbons having at least one nitrogen atom in the hydrocarbon ring, preferably benzimidazole, benzotriazole, Urotropin, 1,5,7-triazabicyclo[4.4.0]dec-5-ene (TBD), 1,8-diazabicyclo[5.4.0]undec-7-ene, 1,5-diazabicyclo[4.3.0]non-5-ene, diazabicyclooctane (DABCO).

These catalytically active substances can either be fixed to a support, preferably a siliceous support, or used directly as catalyst for the disproportionation.

The catalytic disproportionation can be carried out either in the homogeneous phase or in the heterogeneous phase, the reaction on the catalyst being carried out at temperatures from 50° to 350° C. with formation of monosilanes and polysilanes.

In a variant of the invention, the catalyst is a supported catalyst which is characterized by the catalytic component being fixed directly or via a spacer and/or via siloxy groups to the surface of a support material, preferably a siliceous support material.

Suitable siliceous support materials within the scope of the invention include in general all inorganic materials composed of silicon dioxide.

The siliceous support material can be a silicon dioxide material such as silica gel, porous glasses, silicates, silicalites, an aluminum silicate material or a zeolite material, where in the aluminum silicates and in zeolites the catalytic component can optionally in part also be covalently bonded directly (without spacer) or indirectly (with spacer) via Al—OH groups. Optionally, the siliceous support material on which the catalyst of the invention is based can also be a support material which is surface-modified in a known manner.

These supported catalysts are very suitable for heterogeneous catalytic disproportionation since the catalytic component is firmly fixed to an inert support material, which enables easy separation of the products formed from the catalyst and thereby avoids the undesired contamination of the catalytically formed products by catalytically active component.

Preferably, the disilanes to be disproportionated are fed to the catalyst in vapor or gaseous form.

In this preferred procedure, the catalytic conversion is carried out at catalyst temperatures which are above the boiling points of the monosilanes formed as product. In particular, alkylhalodisilanes are reacted at a temperature of at least 100° C., preferably at from 120° C. to 130° C., under protective gas.

If the temperature at the catalyst corresponds to at least the boiling point of the monosilanes formed, then these vaporize immediately after being formed on the catalyst and can be obtained directly by condensation alone without any further isolation measures.

In a further process variant, therefore, the monosilanes formed as product are vaporized as early as during the reaction on the preferably heated catalyst and are thus isolated by distillative separation, while any higher-boiling polysilanes which may be formed in the reaction are fed back into and collected in the liquid phase from which the disilane starting materials for the gas-phase reaction on the catalyst are vaporized.

The polysilanes collected in the liquid phase may, depending on the temperature of the liquid phase, already be partially converted to polycarbosilanes during the distillation and catalytic reaction.

In a further process variant, therefore, the polysilanes contained in the liquid phase are subsequently thermally treated at temperatures up to 400° C. for further conversion into polycarbosilanes and the polycarbosilanes formed are isolated as product. This subsequent treatment can also be carried out in vacuo.

The above-described process for the heterogeneous catalytic disproportionation of disilanes into mono- and polysilanes makes it possible to carry out the process continuously, for example for the workup of disilane-containing distillation residues from the Mueller-Rochow synthesis and for the catalyst-free isolation of the reaction products.

A further advantage of this procedure is, besides the isolation of pure monosilanes, the formation of polymeric reaction products which can be crosslinked to a varying degree and are thus predominantly soluble or no longer soluble in organic solvents. The product can thereby be matched to the further processing desired.

A further preferred procedure for the heterogeneous catalytic disproportionation of silanes comprises contacting the supported catalyst of the invention directly with the disilanes in the reaction vessel. The disproportionation is advantageously carried out under protective gas. The monosilanes formed are distilled off directly during the reaction. The polysilanes remaining in the liquid phase can be readily separated from the catalyst and subsequently thermally treated as described above.

The catalysts of the invention are also directly suitable for the catalytic disproportionation of disilanes without being fixed to a support material. This procedure likewise enables the formation of pure monosilanes. The polysilanes, however, are contaminated by the catalyst component. The disproportionation is preferably carried out under protective gas at from 100° to 350° C.

A common feature of all these process variants is the ability to influence the composition of the disproportionation products in a targeted manner, for example by selection of the catalyst or by appropriate reaction conditions such as temperature, reaction time and amount of catalyst.

The amount of catalyst used is preferably from 0.1 to 10%, the reaction time from 1 to 16 hours.

It has been found that, for example when using imidazole or pyrazole as catalyst, reaction times of from 3 to 4 hours are necessary to form solid polysilane.

Reaction temperatures of about 220° C. are entirely sufficient for obtaining solid products if, for example, imidazole or pyrazole is used as catalyst.

The composition and the consistency of the resulting polysilanes can be varied greatly via the reaction time and the temperature regime. A polysilane prepared at up to 300° C. using imidazole is, for example, a golden yellow, foam-like and very brittle mass. Stopping the reaction at from 200° to 220° C. gives a glassy polysilane which can be remelted and which also has a higher chlorine content than the polysilanes treated at higher temperature.

It is likewise possible to stop the reaction at a stage at which highly viscous polysilanes are present.

The proportion and composition of the monomer fraction can be varied over a wide range by selection of the reaction conditions, the catalyst and the amount of catalyst.

The following examples are intended to illustrate the invention in further detail without restricting its scope. Unless otherwise specified, percentages are always % by weight.

EXAMPLE 1

100 ml of methylchlorodisilane mixture were admixed with 2% of catalyst in a 3-neck flask and heated under protective gas ($N_2$) from room temperature to a maximum of 300° C. The reaction was, if the polysilane formation had not already ended earlier, stopped after about 6 hours. The cleavage products formed were distilled off during the reaction via a 30 cm packed column.

The results of the experiment are shown in Table 1.

EXAMPLE 2

The experimental set-up was analogous to Example 1, but the packed column contained the catalyst fixed to a support and was wrapped with heating tape so that the catalyst was maintained at a temperature of from 100° to 140° C. by means of the heating tape. 100 ml of methylchlorodisilane were likewise initially charged and slowly heated under protective gas from room temperature to a maximum of 350° C. The reaction was ended when the temperature of the polysilane remained above 300° C. for more than 30 minutes, or the temperature at the top of the column indicated that no monomers but only non-cleavable impurities from the disilane fraction, disilanes and low molecular-weight polysilanes were distilling over.

The catalyst used was 3-(4,5-dihydroimidazol-1-yl)-propyltriethoxysilane fixed on silica gel. About 90 ml of monomers and 5 g of polysilane were obtained.

EXAMPLE 3

The experimental set-up was analogous to Example 1. 100 ml of disilane mixture were admixed with 10 g of imidazole fixed on silica gel. The reaction time was 80 minutes, the liquid phase temperature a maximum of 330° C. 77 ml of monomers and 11 g of polysilane/polycarbosilane mixture were obtained.

TABLE 1

| Catalyst | Heating rate °C./min | Reaction time min | Yield Polysilane/polycarbosilane g | Monosilane ml |
| --- | --- | --- | --- | --- |
| TBD | 0.7 | 315 | 20 | 70 |
| Imidazole | 2.3 | 130 | 23 | 60 |
| 1-Methylimidazole | 4.4 | 70 | 21 | 57 |
| 2-Methylimidazole | 5.8 | 45 | 15 | 70 |
| Pyrazole | 0.8 | 250 | 25 | 74 |
| 3-Methylpyrazole | 5.6 | 55 | 11 | 80 |
| DABCO | 4 | 75 | 22 | 62 |

The foregoing description and examples have been set forth merely to illustrate the invention and are not intended to be limiting. Since modifications of the described embodiments incorporating the spirit and substance of the invention may occur to persons skilled in the art, the scope of the invention should be construed to include all variations falling within the ambit of the appended claims and equivalents thereof.

What is claimed is:

1. A process for catalytically disproportionating an aryl- or alkylhalodisilane to form monosilanes and polysilanes comprising contacting the aryl- or alkylhalodisilane at a temperature in the range from 50° C. to 350° C. with a catalyst comprising a nitrogen-containing heterocyclic hydrocarbon having at least one nitrogen atom in at least one 4- to 8-membered hydrocarbon ring, wherein ring atoms adjacent said at least one nitrogen atom are selected from the group consisting of carbon atoms and nitrogen atoms, whereby the aryl- or alkylhalodisilane reacts to form monosilanes and polysilanes, and recovering the resulting monosilanes and polysilanes.

2. A process according to claim 1, wherein said nitrogen-containing heterocyclic hydrocarbon comprises at least one aromatic ring.

3. A process according to claim 1, wherein said nitrogen-containing heterocyclic hydrocarbon comprises at least one non-aromatic ring.

4. A process according to claim 1, wherein said nitrogen-containing heterocyclic hydrocarbon comprises at least one aromatic ring and at least one non-aromatic ring.

5. A process according to claim 1, wherein said at least one nitrogen atom is substituted by a substituent selected from the group consisting of hydrogen, branched or linear alkyl groups, oxygen, halogen, trialkoxysilyl and $NR_2$ wherein R represents hydrogen, linear or branched $C_1$ to $C_6$ alkyl or trialkoxysilyl, or said at least one nitrogen atom is bonded in the ring via 2 δ bonds and 1 π bond or forms a bridgehead to a further ring.

6. A process according to claim 5, wherein said at least one nitrogen atom is substituted by a linear or branched $C_1$ to $C_6$ alkyl group.

7. A process according to claim 1, wherein said ring comprises at least one carbon atom mono- or disubstituted by substituents independently selected from the group consisting of hydrogen, branched or linear alkyl, halogen, oxygen, $NR_2$ wherein R represents hydrogen, linear or branched $C_1$ to $C_6$ alkyl or trialkoxysilyl, and further hydrocarbon ring systems, or said at least one carbon atom forms a bridgehead to a further ring.

8. A process according to claim 7, wherein said at least one carbon atom is substituted by at least one $C_1$ to $C_6$ alkyl group.

9. A process according to claim 1, wherein said heterocyclic hydrocarbon comprises a 5-membered ring containing from 1 to 3 nitrogen atoms.

10. A process according to claim 9, wherein said heterocyclic hydrocarbon is selected from the group consisting of imidazole, 1-methylimidazole, 2-methylimidazole, pyrazole, 3-methylpyrazole, pyrrolidone, N-methylpyrrolidone, triazole, and 1,3dimethyl-2-imidazolidone.

11. A process according to claim 1, wherein said heterocyclic hydrocarbon comprises a 6-membered ring containing at least one ring nitrogen atom.

12. A process according to claim 11, wherein said heterocyclic hydrocarbon is selected from the group consisting of 2,2'-bipyridine, N,N-dibutylpiperazine, and 1,3-dimethyl-3,4,5,6-tetrahydro-2(1H)pyrimidone.

13. A process according to claim 1, wherein said heterocyclic hydrocarbon is a polycyclic hydrocarbon having a ring structure containing at least one ring nitrogen atom.

14. A process according to claim 13, wherein said heterocyclic hydrocarbon is selected from the group consisting of Urotropin, benzimidazole, benzotriazole, 1,5,7-triazabicyclo[4.4.0]undec-5-ene, 1,8-diazabicyclo[5.4.0]undec-7-ene, and 1,5-diazabicyclo[4.3.0]non-5-ene.

15. A process according to claim 1, wherein said catalyst is fixed to a surface of a support material.

16. A process according to claim 15, wherein said catalyst is fixed to the surface of said support material via a spacer.

17. A process according to claim 15, wherein said catalyst is fixed directly to the surface of said support material.

18. A process according to claim 15, wherein said catalyst is fixed to the surface of said support material via siloxy groups.

19. A process according to claim 15, wherein said support material is a siliceous support material.

20. A process according to claim 1, wherein the catalyst is fixed to a support, and the disilanes are introduced in vapor or gaseous form to the catalyst at a temperature of at least 100° C.

21. A process according to claim 10, wherein the reaction is carried out at a temperature in the range from 120° C. to 130° C.

22. A process according to claim 1, wherein monosilanes are recovered by distillative separation during the reaction.

23. A process according to claim 1, further comprising the additional step of subsequently thermally treating the liquid phase containing aryl- or halopolysilane at temperatures up to 400° C. for promoting further conversion into aryl- or alkylhalocarbosilanes.

* * * * *